US00PP08851P

United States Patent [19]

Nicolai

[11] Patent Number: Plant 8,851

[45] Date of Patent: Aug. 2, 1994

[54] JONAGOLD APPLE TREE: JORED VARIETY

[75] Inventor: Johan Nicolai, Sint-Truiden, Belgium

[73] Assignee: N.V. Jo Nicolai & Co., Sint-Truiden, Belgium

[21] Appl. No.: 106,600

[22] Filed: Aug. 16, 1993

[51] Int. Cl.[5] ..... A01H 5/00

[52] U.S. Cl. ..... Plt./34.1

[58] Field of Search ..... Plt. 34.1

[56] References Cited

PUBLICATIONS

Goddrie, P. D., et al., "Jonagold Color Varieties" Brochure, Sep. 25, 1990 Fruit Cultivation Test Station, Wilhelminadorp, Belgium, pp. 1–29.

"Report on Technical Examination. The Plant Variety Rights' Office—United Kingdom Feb. 25, 1992".

Copy of the Breeder's Rights Document No. F0559 issued by the Belgium government on Jun. 26, 1992 with respect to the new apple variety JORED.

Schedule of sales of the apple variety JORED in the U.S.A. by applicant's U.S.A. affiliate Treco Co. of Woodburn, Oreg.

Sales contract with the vendees.

*Primary Examiner*—James R. Feyrer

*Attorney, Agent, or Firm*—Eugene D. Farley

[57] ABSTRACT

The Jored strain of Jonagold apple tree characterized by the clear, bright red on a bright yellow-green background color of its fruit, substantially without stripes or bands; by the early finish color development of its fruit; by the conical contour of its fruit; and by the prominence of its lenticels.

7 Drawing Sheets

This invention relates to a new and distinct variety of apple tree which heretofore has been variously named Jored
King Jonagold
Red Jonagold Of the foregoing names, the latter two have been abandoned in favor of the name Jored.

The circumstances relating to the discovery of my new apple tree variety are as follows:

I discovered the new variety of apple tree Jored in my cultivated apple orchard located at Ter Weiden, Belgium in the summer of 1979.

During an inspection of the orchard, I noticed a single limb mutation which had developed as a side branch at the bottom of a standard Jonagold apple tree. Jonagold is an unpatented variety which is a well-known cross between the Jonathan and Golden Delicious apple tree varieties.

The single limb mutation which was the subject matter of my observation was characterized by the presence of apples colored over about 70–90% of their surface with a solid bright red blush on a bright green-yellow background, substantially without stripes. This was unique, since the apples on all of the other branches of the tree were characterized by the standard Jonagold coloring; that is, a bright, wine red with white to yellow background, the red color being evident under small stripes (chimaeres). It also made the apples highly desirable on the market place, because of their unusual and attractive appearance.

In 1979 I made separate cuttings from the limbs on the branch mutation, resulting in seven specimens which it was my plan to judge separately in generation 1 (F1) and generation 2 (F2).

In 1982 trees of the F2 generation were planted in two locations:

The first was my orchard in Gorsem (Sint-Truiden) Belgium.

The second (by error) was in the orchard of Mr. Vanderstukken-Nijns in Geetbets, Belgium.

In 1985 in the Vanderstukken-Nijns orchard a tree was noted bearing apples having the before-noted color characteristics—a solid, bright red blush over about 70–90% of the fruit surface, on a bright, green-yellow background, substantially without stripes. This tree was made the subject of a plant breeder's rights application in Belgium under the name of Jored.

In 1986 I noted among the trees which had been planted in my orchard in Gorsem (Sint-Truiden) Belgium an equally well colored Jonagold tree of identical characteristics. This tree was made the subject matter of an application for plant breeder's rights in Belgium in October of 1986 under the name King Jonagold.

Because of the identical characteristics of Jored and King Jonagold, and their common parentage (the single limb sport of the Jonagold apple tree which I discovered in my Ter Weiden orchard in 1979), the Plant Breeder's rights authorities in 1992 granted to me Plant Breeder's rights for Jored in Belgium. At the same time, the same authorities refused to grant Plant Breeder's rights for King Jonagold because of the identity of the specimens.

In 1989 I bought from Vanderstukken-Nijns any rights he might have to the variety Jored and transplanted the trees bearing this name to my test orchard in Gorsem (Sint-Truiden) Belgium.

Subsequently, I applied for Plant Breeder's rights for Jored in Denmark, France, Germany, Italy, The Netherlands, Switzerland and the United Kingdom.

Accordingly, the Breeder's Rights filing on the Jonagold apple variety Jored as of the year 1992 are as follows:

| COUNTRY | APPLICATION NO. | APPLICATION DATE |
|---|---|---|
| Belgium | F0559 | 8 October 1985 |
| Denmark | 3535 | 19 June 1992 |
| France | 11599 | 30 April 1992 |
| Germany | APF87 | 11 May 1992 |
| Italy | 149 NV/92 | 22 June 1992 |
| Netherlands | APP 163 | 29 April 1992 |
| Switzerland | 92-20-817 | 12 May 1992 |
| U.K. | APF87 | 2 June 1992 |

In Belgium, application No. FO559 issued on Jun. 26, 1992 as Certificate No. 0837.

Additionally, Jored is one of only five Jonagold varieites, out of a total of 70 or 80 Jonagold varieties, that has been granted UPOV recognition.

In the report on Technical Examination issued by the U.K. Plant Variety Right's Office, the subject apple variety is identified as "Red Jonagold". This is an early name for the variety, now abandoned in favor of Jored.

In connection with the above noted Breeder's Rights Program, the new apple tree variety Jored has been asexually propagated through four generations. Its new characteristics have been shown to be stable and reproduceable.

The new characteristics which characterize Jored are color, early development of color, the conical contour of its fruit and the character of its lenticels.

With respect to color, its color uniqueness has been defined by the U.K. Plant Variety Right's Office in its report on Technical Examination of Jored carried out at the request of the Belgium Breeder's Rights Office as being "a clear bright red, without stripes or bands". There may, however, be a few pale, small, chimaera stripes. This color extends over about 80%, broadly about 70–90% of the fruit surface. Its Royal Horticultural Colour Chart of London (RHCCL or more frequently, RHS) color definition is 45 B. This compares with the RHCCL color definition of standard Jonagold, which is 44 B. Additionally, the apple is characterized by a sharply contrasting, bright green-yellow background color having a RHCCL color value of 150 B/C.

Jored differs from the other more significant (granted Plant Breeder's Rights for European countries or plant patent rights for the U.S.A.) color sports of Jonagold in the following respects:

Jored: a clear bright red, substantially without stripes or bands.

New Jonagold: Color characteristics identical to standard Jonagold, but with many big chimaera stripes.

Jonagored: dark red, with many stripes.

Crowngold: RHCCL color definition is 44B; no prominent lenticels; many chimaera stripes and many trees or branches with the same color characteristics as standard Jonagold.

Rubinstar: Very dark red; no chimaera stripes; a few lenticels.

Daliquy: Color characteristics are not different from standard Jonagold. In Europe it is considered as a standard Jonagold.

Jonica: Color is more brownish red; a few lenticels.

Jonagold De Coster: Dark red without stripes.

With respect to early color development, Jored has been observed to develop its finished color about 5 days earlier than do standard Jonagold fruits. Jored apples do not mature earlier than standard Jonagold apples. However, if picked on the basis of color performance the Jored apples may be harvested about 5 days earlier. This feature is of particular importance in areas having short growing seasons.

With respect to fruit shape, Jored apples have a more conical shape than do the fruits of the above identified Jonagold sports. This characteristic is particularly apparent in the case of Jored apples having a diameter range of from 70–85 mm. If height/width averages are made for the complete production (all diameter ranges), differences between the sports become less evident. However, the general appearance of a bulk quantity of Jored apples makes their more conical shape clearly apparent.

The foregoing characteristics of Jored apples, coupled with their other desirable qualities, have materially increased the market value of the fruit. Jored apples consistently command a higher price on the market place than do the other Jonagold varieties. This is indicated by the results of sales at the annual auctions of the Belgische Fruitveiling C.V., an association of 6,000 fruit producers from the various important cultivation regions of Belgium, which distributes about 45% of all fruit offered at Belgium auctions from year to year, including about 55% of all Jonagold apples. The comparative results for the seasons 90/91 and 91/92 are as follows:

THE SPORTS OF JONAGOLD COMPARISON OF SALES AND PRICES, SEASONS OF 90/91–91/92

| VARIETY | SALES 90/91 | SALES 91/92 | PRICE Belgian Francs per kilo 90/91 | PRICE Belgian Francs per kilo 91/92 |
|---|---|---|---|---|
| JONAGOLD | 28.834.740 | 20.322.137 | 21,17 | 40,64 |
| JONA-GORED | 6.637.572 | 1.835.508 | 22,63 | 39,74 |
| NOVAJO | 38.800 | 147.056 | 23,96 | 41,67 |
| JONICA | 28.686 | 228.201 | 23,91 | 41,03 |
| JORED | 2.080 | 228.135 | 29,81 | 46,32 |
| NEW JONAGOLD | 21.684 | 4.860 | 24,88 | 41,96 |

With respect to lenticels, the lenticels of Jored are particularly prominent. Unlike standard Jonagold, Jonagored and Jonagold Decoster, the Jored lenticels are very prominent. They are larger and of a distinct white color.

| | Height (mm.) | Width (mm.) | Height/Width (Average) |
|---|---|---|---|
| Jonagold Decoster | 69,38 | 78,78 | 0,88 |
| Jonagored | 69,70 | 77,22 | 0.90 |
| Jored | 78,3 | 75,16 | 1,04 |

Based on selective samples of 5 apples.

A botanical description in greater detail of my new apple tree variety and other fruit follows. The description is made with particular reference to the drawings comprising comparative photographs of Jored vs. Standard Jonagold, grown under the same conditions in neighboring orchards, wherein FIGS. 1 and 2 are comparative views of Jored (FIG. 1) and Standard Jonagold (FIG. 2) taken on Sep. 2, 1992 and illustrating the pronounced advanced coloration of Jored on that early date.

Figure 1:
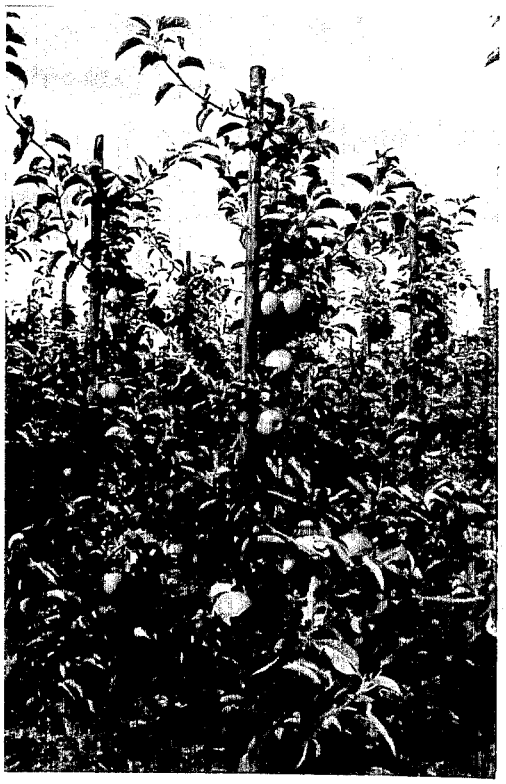
Figure 2:
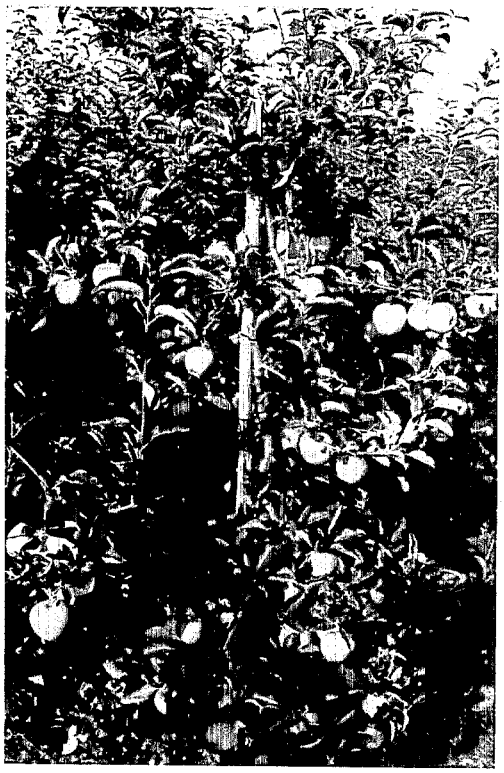
Figure 3:
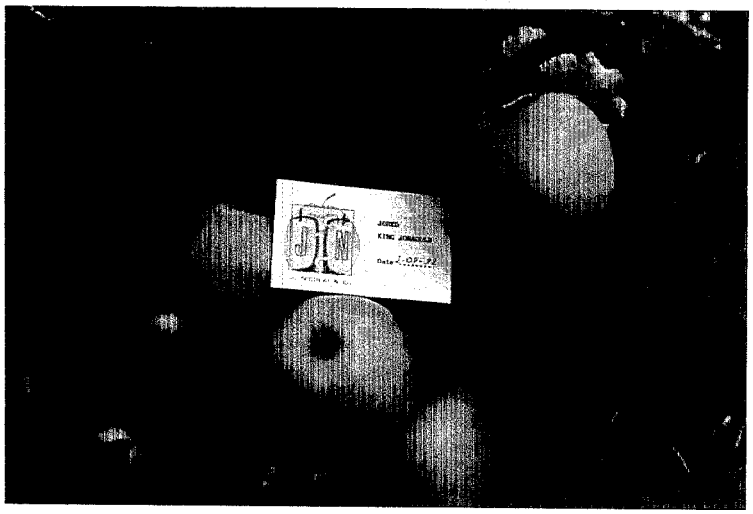
FIGS. 3 and 4 are similar views taken on an enlarged scale, FIG. 3 being of Jored and FIG. 4 of Standard Jonagold.
Figure 4:
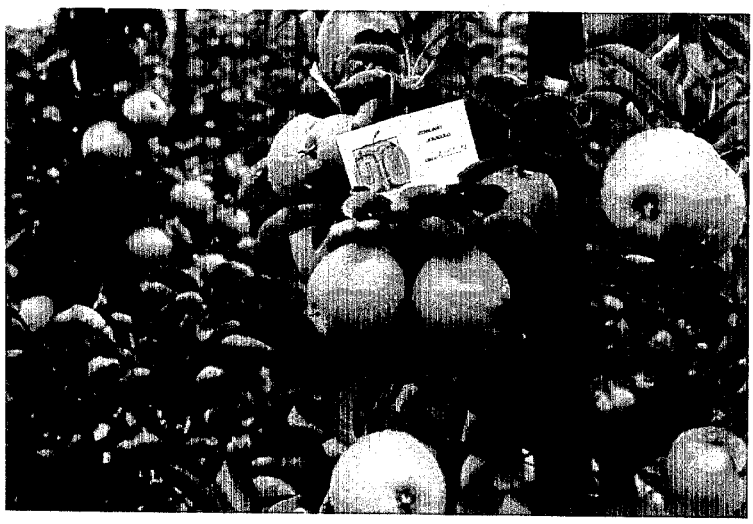
Figure 5:
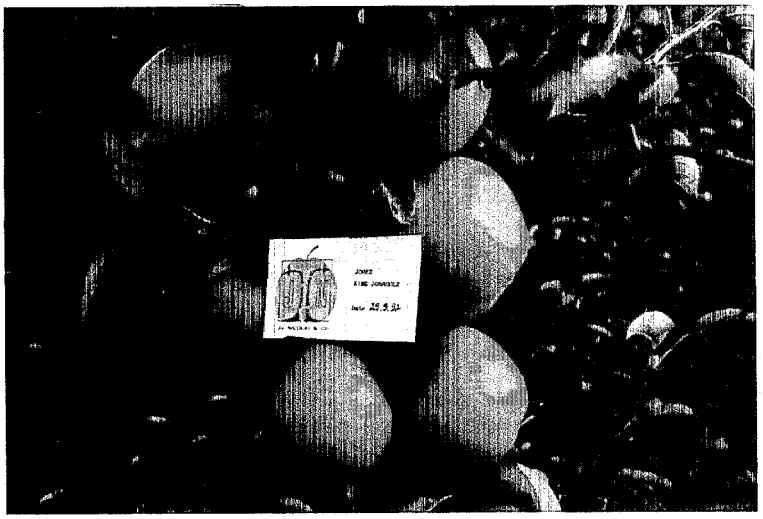
FIGS. 5 and 6 are views on an enlarged scale of Jored (FIG. 5) and Standard Jonagold (FIG. 6) illustrating the solid, bright red color and the absence of stripes characterizing the mature Jored fruit, as compared with Standard Jonagold, both views being taken on Sep. 23, 1992.
Figure 6:
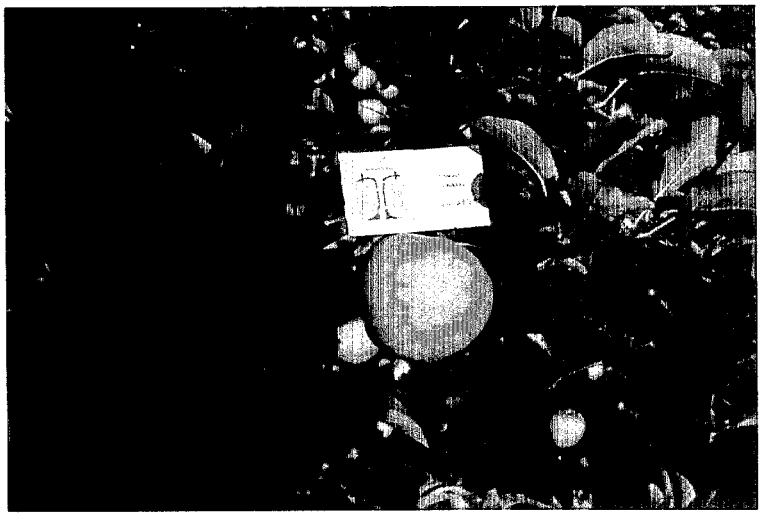
Figure 7:
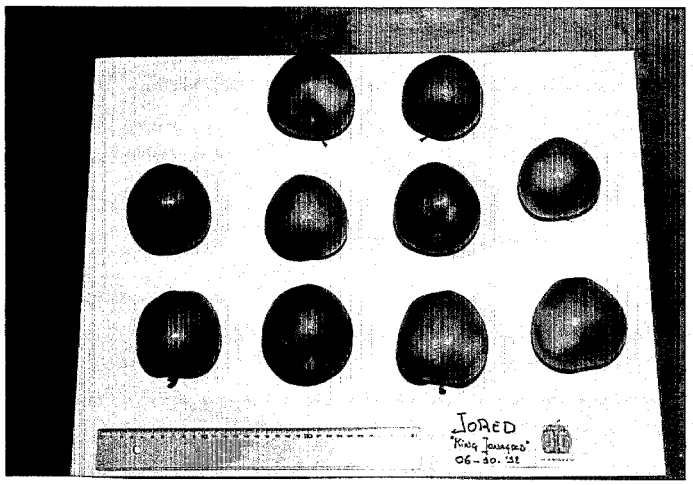
FIGS. 7 and 8 are views of mature Jored fruits taken on Oct. 6, 1992 and illustrating the color characteristic of the fruit, with particular reference to the yellow-green background coloration.
Figure 8:
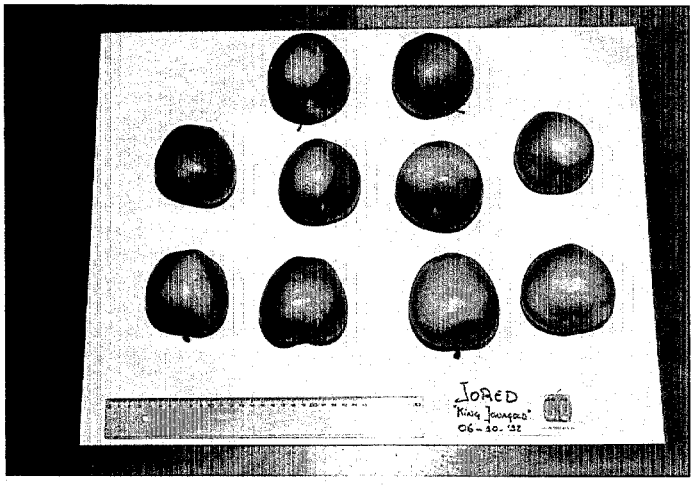
Figure 9:
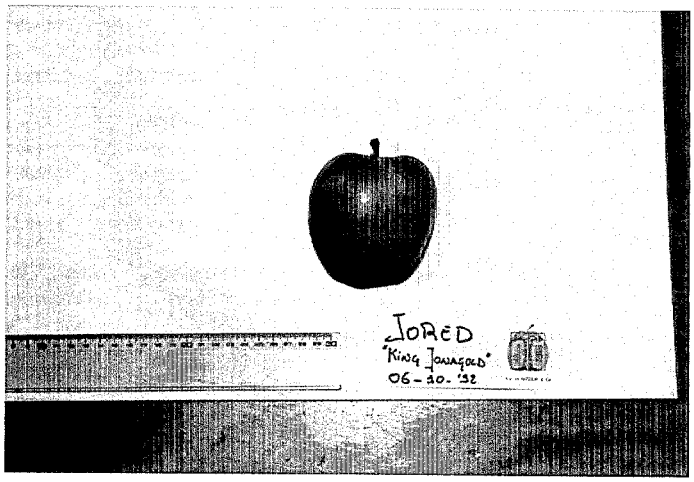
FIG. 9 is a further view of the Jored fruit, taken on Oct. 6, 1992 and illustrating its characteristic color.
Figure 10:
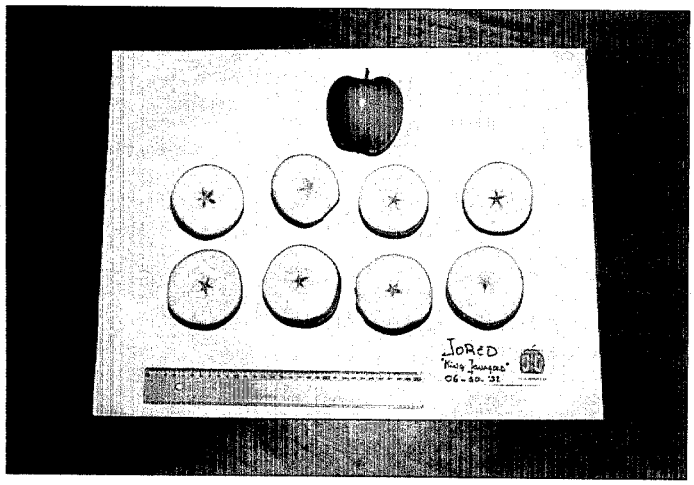
FIG. 10 is a sectional view of Jored, the mature fruit on Oct. 6, 1992.
Figure 11:
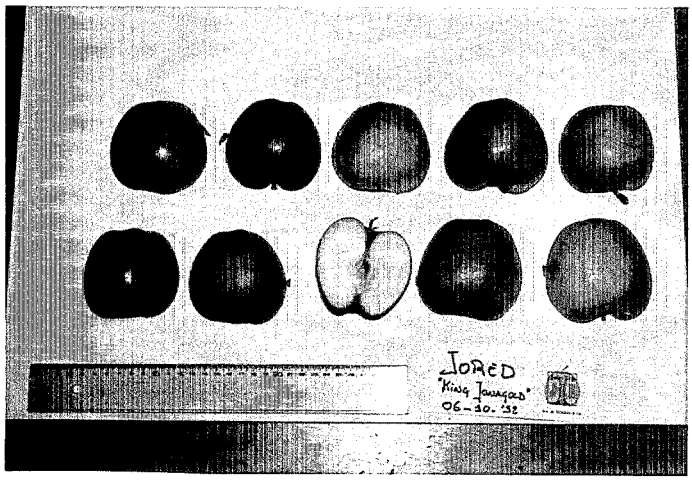
FIGS. 11 and 12 are views of the fruit in longitudinal section, illustrating its elongated, conical contour.
Figure 12:
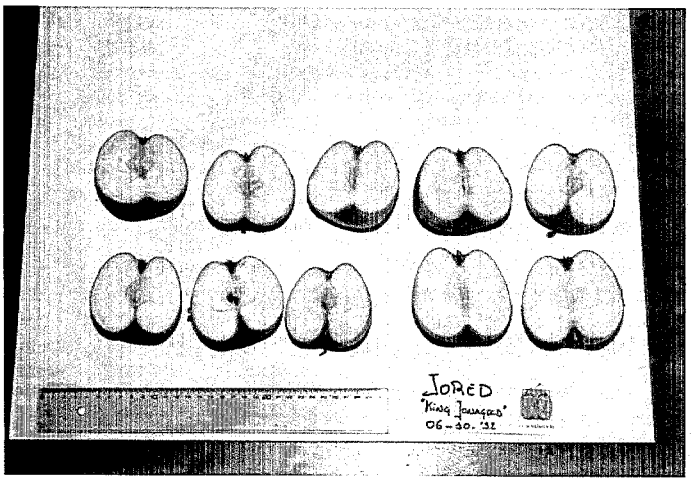
Figure 13:
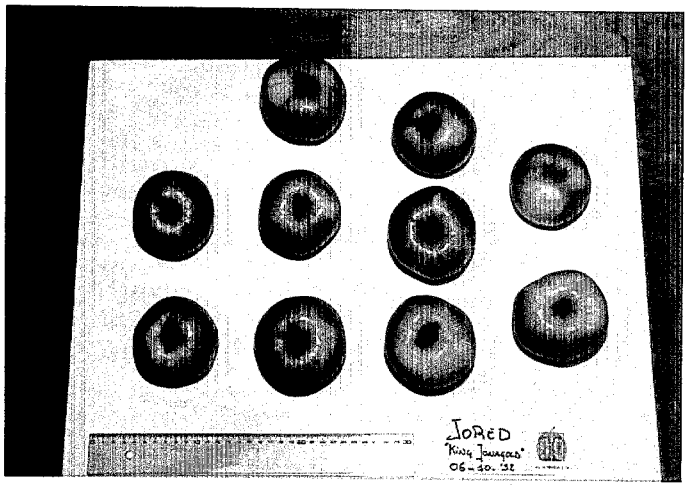
FIGS. 13 and 14 are top and bottom views, respectively, further illustrating the contrasting color characteristic of the fruit skin.
Figure 14:
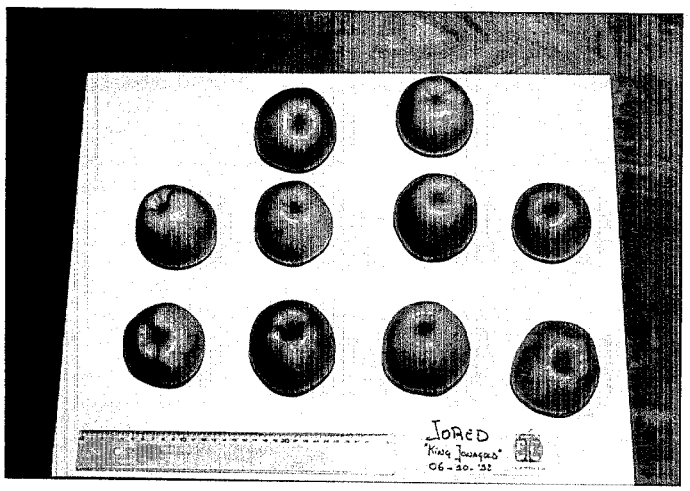

In greater detail, the characteristics of the newly discovered apple tree variety Jored are as follows:

Tree: Medium size, vigorous, upright, hardy, very productive, regular bearer, spreading. The habit of the Jored tree is substantially similar to that of standard Jonagold and the other color sports of Jonagold. A virus-free Jored tree grows as vigorously as does a standard Jonagold tree or as any other virus-free Jonagold sport tree, if they are compared under the same growing conditions and are grown on the same rootstock. Special pruning training and thinning procedures are not required for Jored (see NPGF (Nationale Proeftuin Voor Grootfruit VZW, Sint-Truiden Research Station, Jaarverslag 1992, 1992 Report). The manner of formation and appearance of the fruiting spurs of Jored and the bearing habit on the fruiting spurs and one-year old shoots are the same as for other Jonagolds.

*Bark.*—Comparisons of the bark of the Jored tree with the bark of standard Jonagold and other Jonagold sports indicates that it is impossible to find any differences in color of the bark. It also is impossible to find any differences in the bark lenticels.

Predominance of bearing: On spur.

Dormant one year old shoot: Strong pubescence on upper half of shoot; thick at center.

Lenticels: Few-medium in number, but prominent.

Leaves:

*Size.*—Large to very large. The length/width ratio of the fourth-sixth fully expanded leaf is medium.

*Upper side.*—Strongly glossy.

*Lower side.*—Medium pubescence.

*Lamina length.*—84 mm.

*Lamina breadth.*—63 mm.

*Lamina LIB ratio.*—1.33.

*Petiole length.*—21.

In general, the leaves and stipules of Jored do not differ from those of standard Jonagold or the other Jonagold clones. Jored occasionally is characterized by the presence of stipules of medium size, at the base of large leaves, on vigorous shoots.

Flowers: Time of flowering: Medium-about the end of April in Belgium, as with standard Jonagold. A detailed study of the blooming stages of Jonagold sports, with specific reference to the white cluster, full bloom, and end of flowering stages, for 28 Jonagold sport varieties including Jored, indicates the blooming stages to be either identical or within a day or two of each other. In this study, Jored demonstrates a white cluster stage date of April 18th, a full bloom date of May 4 and an end of flowering date of May 16th. It has been observed that Jored demonstrates a difference in flower development in the pre-balloon stage, but none at white bud. This distinction is to be observed in detail during the flowering season of 1994.

*Pedicels.*—Red.

*Stamens.*—Dark-red and pressed against the sepals after flowering.

Petals: Position of margins, touching; color of upper side, streaked with white (RHCCL, 63 C).

Flower size: With the petals pressed into horizontal position the flower size is from small to medium.

Fruit: Specimens described were grown and observed at the Plant Variety Rights Office, Brogdale EHS, United Kingdom. They are identical to former observations in Jo Nicolai's test orchard in Gorsem, Belgium.

*Size.*—Uniform, large fruit, height 78.3 mm.

*Shape.*—Conical, global, symmetric in side view.

*Skin.*—Tough, smooth, glossy, medium thickness.

*Lenticels.*—More numerous, larger in size, and of higher density than in the case of standard Jonagold; of a distinct white color; striking in appearance. However, the Jored lenticels are not raised above the surface of the fruit skin. They cannot be detected by touch more easily than can the lenticels of other Jonagold sports. A comparison follows (average values):

| | JORED | Other Jonagold sports & standard Jonagold |
|---|---|---|
| number of lenticels/cm$^2$ | 14 | 8 |
| size of lenticels | 1 mm$^2$ | 0,5 mm$^2$ |
| color of lenticels | white | grey |

*Color.*—Green during the earlier stage of immaturity becoming at maturity a clear bright red blush (RHCCL 45B) over about 70–90% of the fruit surface, without stripes or bands, on a bright green-yellow ground surface (RHCCL 150 B/C). Although the color formation is intense, Jored remains a bi-colored variety: a bright red blush on a green ground color. 100% of the fruits which are exposed directly to sunlight (as compared with 75% for standard Jonagold) develop full color. About 35% of the fruits which are not directly exposed to sunlight, color sufficiently to be classified as class 1 fruit (as compared with 0% for standard Jonagold). Class 1 fruits are defined as fruits having at least 30% of the fruit surface covered with a bright red blush. A study made by the research station for pit fruit in Belgium (Nationale Proettuin voor Grootfruit — N.P.G.F. — Fruittuinweg 1 — Sint-Truiden) indicates that, of 19 Jonagold varieties, only Jored and Jonica are in the group of Jonagold sports with the same red blush as standard Jonagold. However, Jored differs from standard Jonagold in that the color formation for standard Jonagold is in the form of small stripes whereas that for Jored is block-type. Jonica initiates its color formation with a brown-red color. Crown gold is characterized by irregular color formation and small stripes. Hence it is of very little interest in Belgium and Holland. Jonagored and Rubinstar are dark red, full colored mutants. They start coloring in July and finish with a dark red color. Jonagold "De Coster" shows a red to dark red, striped coloration on a large portion of its surface. Standard Jonagold, Daliguy and Crowngold start coloring with many small stripes which form with the blush. Jored and Jonica start coloring in August, with a uniform coloration. They change into red: bright red for Jored, brown red for Jonica, as the ripening season progresses. They demonstrate only a few very small chimaera stripes. Jonagored, Jonagold "De Coster", New Jonagold, Crowngold, standard Jonagold, Daliguy are unique in coloring striped. They have a much different appearance from Rubinstar, Jored, and Jonica, which color uniformly. Jonagored and Rubinstar are full colored clones which are completely different in color formation and final color, as compared with the blush type, bi-colored clones (Jored and Jonica). Chimaera Stripes (Chimaeres): Uniformly colored fruits can also show some chimaeres. When these are very small, they don't interrupt the uniformity and general appearance of the blush color. In a small percentage of instances, Jored apples, demonstrate very small chimaeres (1 to 2 mm in width and a few mm long). However, these chimaeres are negligible and do not compare, for example, with the wide and numerous chimaeres of new Jonagold. Background color: The green background color which is typical of Jored is caused by the fact that Jored colors well before its ripening stage starts. This means that a big percentage of Jored apples can be picked in an optimum stage, i.e. at a stage in which they demonstrate a bright red blush on a green background. Under good storing conditions, this green background color can be retained for as much as 8 months before it turns into yellow. This distinguishes from standard Jonagold, Daliguy, Jonica, New Jonagold and Crowngold, which do not follow this pattern. They only can be picked when they are ripe, at a stage at which the background color already is more yellow. The green background color which is typical of Jored is caused by the fact that Jored colors well before its ripening stage starts. This means that a big percentage of Jored apples can be picked in an optimum stage, i.e. at a stage in which they demonstrate a bright red blush on a green background color. Under good storing conditions, this green background color can be retained for as much as 8 months, before it turns into yellow. This compares with standard Jonagold, Daliguy, Jonica, New Jonagold and Crowngold which do not follow this pattern. They only can be picked when they are more ripe, at a stage at which the background color already is more yellow.

*Seeds.*—5–8, perfect; not over 2 per cell. Length, 1 cm. Breadth ½ cm.

*Form.*—Acute.

*Color.*—Chestnut, auburn.

*Flesh.*—Juicy, creamy in color, medium firm, crisp in texture; sweet/sour in flavor.

*Internal fruit characteristics.*—As indicated by work done at the Research Station for Pitfruit (Ste-Truiden) NPGF, the fruit of Jored is very firm with a high acid content and the highest sugar content of any of the four prominent varieties tested: Jored (King), Jonagored, Rubinstar and New Jonagold.

Comparisons of firmness, sugar content and acidity follow.

COMPARISON OF FIRMNESS

| Mutant | Year 1990 kg/0,5 cm² | Year 1991 kg/0,5 cm² | Year 1992 kg/0,5 cm² |
|---|---|---|---|
| JONAGORED | 4,0 | 5,1 | 7,8 |
| RUBINSTAR | 4,9 | 4,8 | 7,6 |
| NEW JONAGOLD | 4,1 | 4,9 | 7,5 |
| KING JONAGOLD (JORED) | 4,9 | 4,9 | 7,8 |

COMAPRISON OF SUGAR CONTENT (% Brix)

| Mutant | Year 1989 % Brix | Year 1990 % Brix | Year 1991 % Brix | Year 1992 % Brix |
|---|---|---|---|---|
| JONAGORED | 15,1 | 13,9 | 15,4 | 12,6 |
| RUBINSTAR | 16,0 | 11,2 | 15,4 | 12,8 |
| NEW JONAGOLD | 15,1 | 14,4 | 15,9 | 13,6 |
| KING JONAGOLD (JORED) | 16,9 | 15,4 | 15,9 | 14,2 |

COMPARISON OF ACIDITY ml NaOH necessary to introduce a decoloration of phenolphthalein indicator in 10 ml juice of the fruits

| Mutant | Acidity 1989-ml | Acidity 1990-ml | Acidity 1991-ml | Acidity 1992-ml |
|---|---|---|---|---|
| JONAGORED | 10,3 | 9,4 | 13,7 | 10,3 |
| RUBINSTAR | 10,1 | 8,9 | 12,3 | 9,3 |
| NEW JONAGOLD | 8,9 | 8,1 | 12,5 | 9,7 |
| KING JONAGOLD (JORED) | 12,5 | 10,4 | 13,2 | 9,9 |

*Core.*—The core-line is medium distinct.

*Stem.*—Slender.

*Cavity.*—Symmetrical. Depth 17.9 mm.: width 36.8 mm.

*Basin.*—Symmetrical. Width: 30.3; height 78.3.

*Use.*—Culinary; juice; primarily for dessert.

*Keeping quality.*—Good, up to 7 months in CA-storage, 9 to 12 months in ULO-storage, about the same as Golden Delicious.

I claim:

1. The new and distinct variety of Jonagold Apple Tree, Jored, substantially as herein shown and described, characterized particularly by the clear, bright red color of its fruit over about 70–90% of the fruit surface, on a bright yellow-green background, substantially without stripes or bands; by the early finish color development of its fruit; by the conical contour of its fruit; and by the prominence of its lenticels.

* * * * *